(12) United States Patent
Hahn et al.

(10) Patent No.: US 10,399,291 B2
(45) Date of Patent: Sep. 3, 2019

(54) SMART CONTACT LENSES AND SMART GLASSES

(71) Applicant: PHI BIOMED CO., LTD., Seoul (KR)

(72) Inventors: Sei Kwang Hahn, Pohang (KR); Young Chul Sung, Seoul (KR); Beom Ho Mun, Daejeon (KR); Keon Jae Lee, Daejeon (KR); Dohee Keum, Busan (KR); Su Jin Kim, Seoul (KR)

(73) Assignee: PHI BIOMED CO., LTD., Seoul (KR)

( * ) Notice: Subject to any disclaimer, the term of this patent is extended or adjusted under 35 U.S.C. 154(b) by 0 days.

(21) Appl. No.: 15/522,816

(22) PCT Filed: Apr. 25, 2016

(86) PCT No.: PCT/KR2016/004295
§ 371 (c)(1),
(2) Date: Apr. 28, 2017

(87) PCT Pub. No.: WO2016/171529
PCT Pub. Date: Oct. 27, 2016

(65) Prior Publication Data
US 2018/0036974 A1    Feb. 8, 2018

(30) Foreign Application Priority Data

Apr. 24, 2015 (KR) ........................ 10-2015-0058154

(51) Int. Cl.
*G02C 7/00* (2006.01)
*G02C 13/00* (2006.01)
(Continued)

(52) U.S. Cl.
CPC .... *B29D 11/00096* (2013.01); *A61B 5/14532* (2013.01); *A61B 5/4839* (2013.01);
(Continued)

(58) Field of Classification Search
CPC .... B29D 11/00826; G02B 1/043; G02C 5/00; G02C 7/04; G02C 7/08; A61K 9/0051;
(Continued)

(56) References Cited

U.S. PATENT DOCUMENTS 8,268,536 B2    9/2012    Lee
8,414,912 B2    4/2013    Ciolino
(Continued)

FOREIGN PATENT DOCUMENTS

JP    2000-507814    6/2000
JP    2004-517858    6/2004
(Continued)

OTHER PUBLICATIONS

C. L. Rowe-Rendleman et al., "Drug and Gene Delivery to the Back of the Eye: From Bench to Bedside", Investigative Opthalmology & Visual Science, vol. 55, No. 4, Apr. 28, 2014, p. 2714.
(Continued)

*Primary Examiner* — Dawayne Pinkney
(74) *Attorney, Agent, or Firm* — Lex IP Meister, PLLC

(57) ABSTRACT

The present invention provides a smart contact lens including a sensor capable of non-invasively sensing an eye disease in real time and a drug reservoir, and smart glasses for controlling the smart contact lens.

21 Claims, 17 Drawing Sheets

(51) Int. Cl.
  *A61F 2/00* (2006.01)
  *B29D 11/00* (2006.01)
  *A61K 39/395* (2006.01)
  *A61M 37/00* (2006.01)
  *A61F 9/00* (2006.01)
  *G02C 7/04* (2006.01)
  *A61B 5/145* (2006.01)
  *A61B 5/00* (2006.01)
  *G01N 33/52* (2006.01)
  *G01N 33/543* (2006.01)
  *G01N 33/66* (2006.01)
  *G02B 27/01* (2006.01)
  *G02C 7/08* (2006.01)
  *A61K 9/00* (2006.01)

(52) U.S. Cl.
  CPC .......... *A61B 5/6821* (2013.01); *A61F 9/0017* (2013.01); *A61K 39/395* (2013.01); *A61M 37/00* (2013.01); *G01N 33/528* (2013.01); *G01N 33/5438* (2013.01); *G01N 33/66* (2013.01); *G02C 7/04* (2013.01); *A61K 9/0048* (2013.01); *G01N 2800/164* (2013.01); *G02B 2027/0178* (2013.01); *G02C 7/085* (2013.01); *G02C 7/086* (2013.01)

(58) Field of Classification Search
  CPC ...... A61K 9/0009; A61K 9/19; A61K 31/085; A61K 31/4164; A61K 31/573; A61K 9/0048
  USPC ...... 351/159.33, 41, 159.02, 159.03, 159.39, 351/159.4, 159.78, 178, 160 R; 424/427–429
  See application file for complete search history.

(56) References Cited

U.S. PATENT DOCUMENTS

| | | | |
|---|---|---|---|
| 2003/0170209 A1* | 9/2003 | Abitbol | A61K 38/2257 424/93.2 |
| 2005/0096587 A1 | 5/2005 | Santini, Jr. et al. | |
| 2013/0045927 A1* | 2/2013 | Dana | C07K 16/22 514/20.8 |
| 2014/0190839 A1 | 7/2014 | Liu | |

FOREIGN PATENT DOCUMENTS

| | | |
|---|---|---|
| JP | 2009-519715 | 5/2009 |
| JP | 2011-517659 | 6/2011 |
| JP | 2011-519711 | 7/2011 |
| JP | 2013-543380 | 12/2013 |
| JP | 2014-028141 | 2/2014 |
| JP | 2014-506119 | 3/2014 |
| JP | 2015-035357 | 2/2015 |
| KR | 10-2011-0127658 | 11/2011 |
| WO | 2014-110492 | 7/2014 |
| WO | 2015-035357 | 3/2015 |
| WO | 2015/035357 | 3/2015 |

OTHER PUBLICATIONS

N. M. Farandos et al., "Contact Lens Sensors in Ocular Diagnostics", Advanced Healthcare Materials, vol. 4, No. 6, Nov. 17, 2014, pp. 792-810.

S. K. Hahn et al., "Smart contact lens and smart eye glasses", Frontiers in Bioengineering and Biotechnology, vol. 4, Mar. 30, 2016.

JPO, Office Action of JP 2018-507476 dated Nov. 19, 2018.

EPO, European search report of EP 16783461.3 dated Nov. 22, 2018.

* cited by examiner

[FIG. 1a]
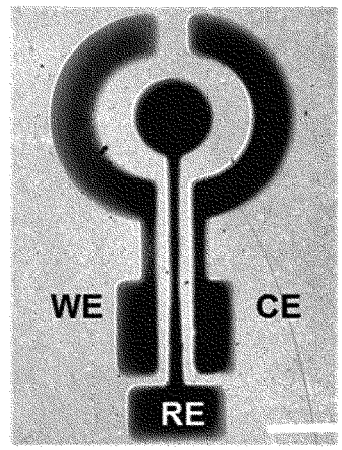
[FIG. 1b]
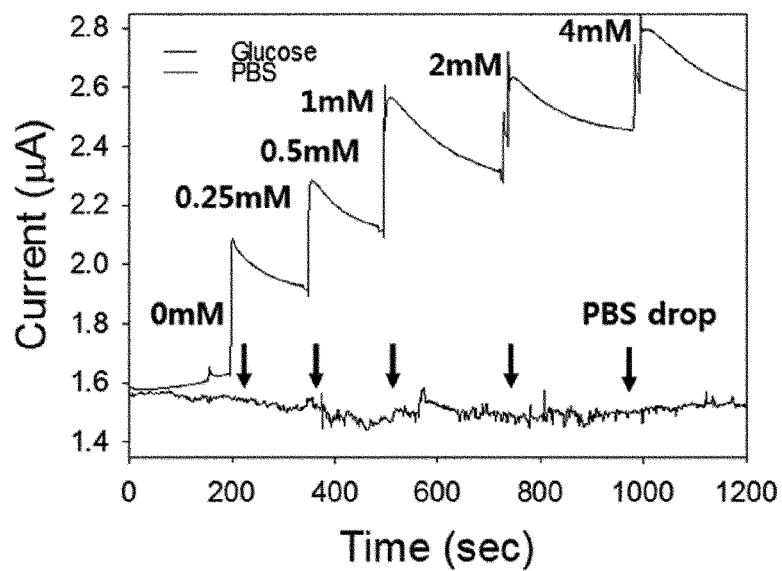

[FIG. 1c]
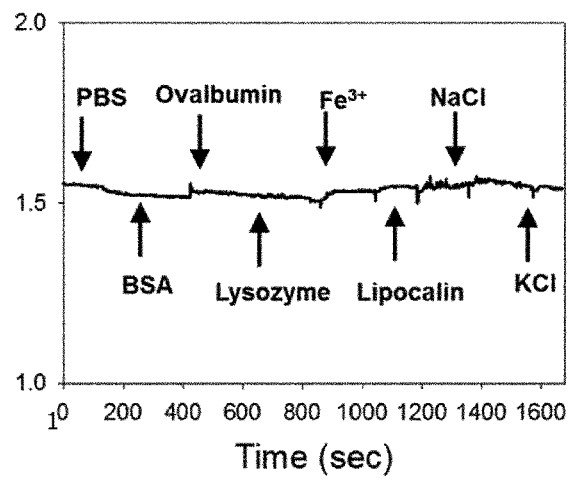
[FIG. 2a]
[FIG. 2b]
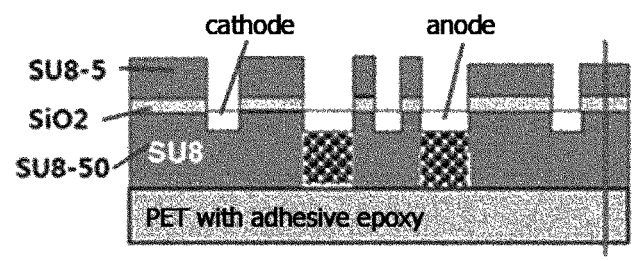

[FIG. 2c]
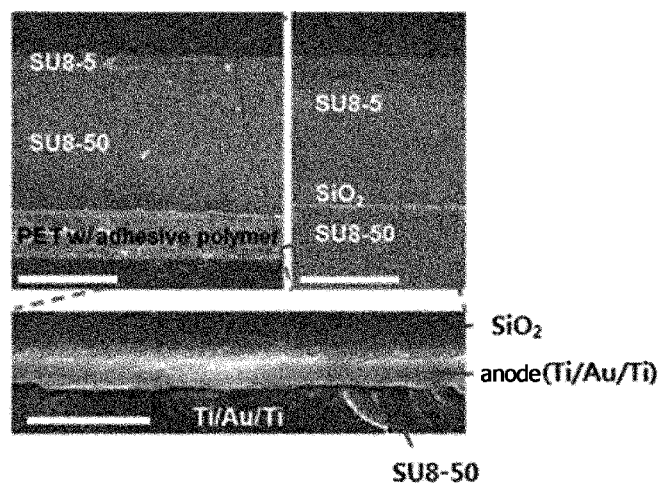
[FIG. 3a]
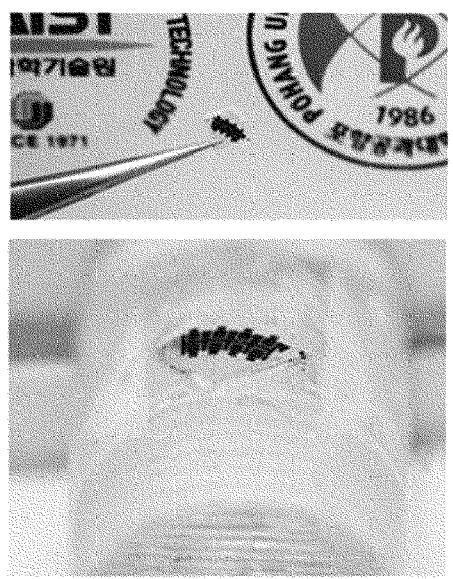

[FIG. 3b]
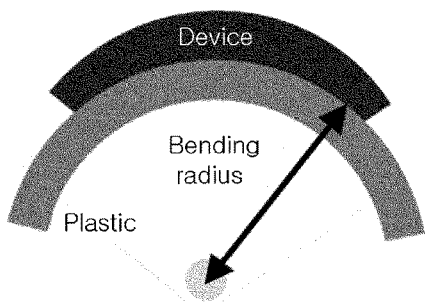
[FIG. 3c]
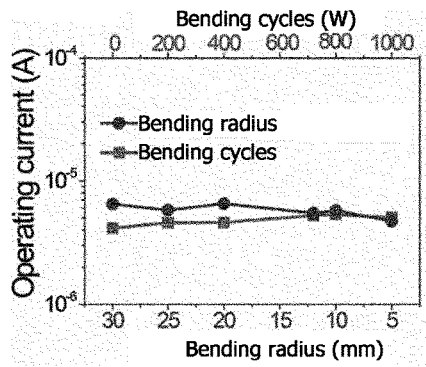
[FIG. 3d]
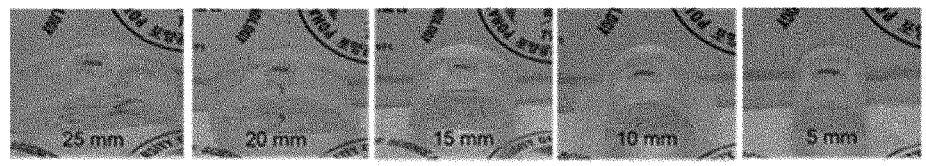

[FIG. 4a]
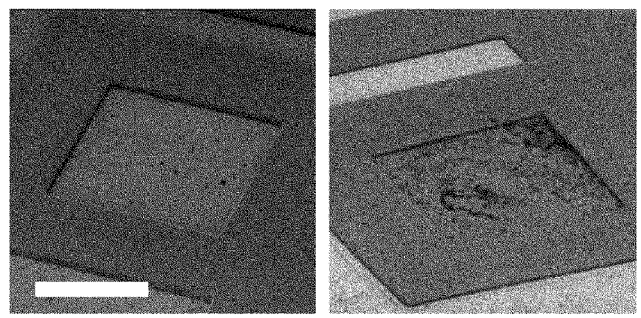
[FIG. 4b]
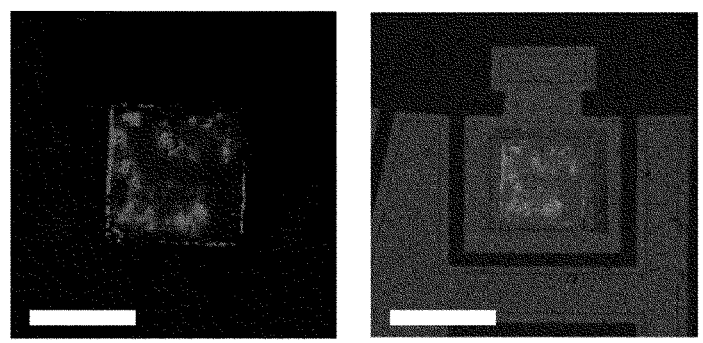

[FIG. 4c]
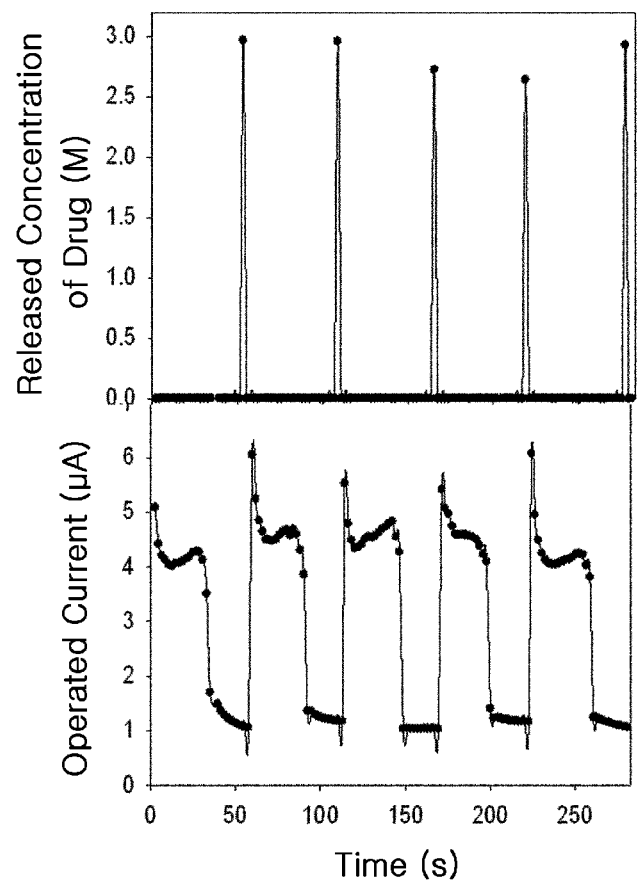

[FIG. 4d]
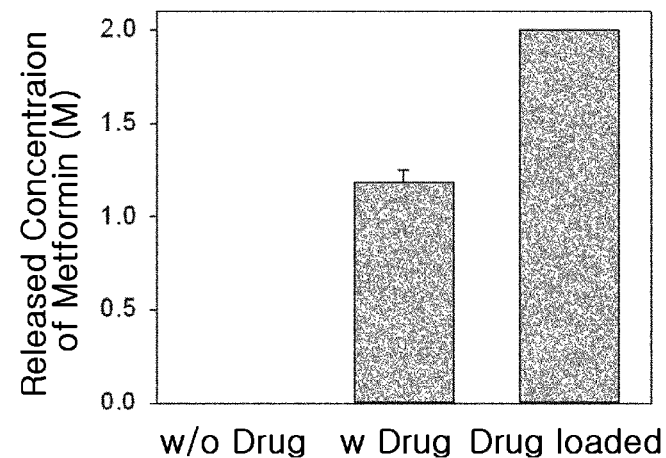
[FIG. 4e]
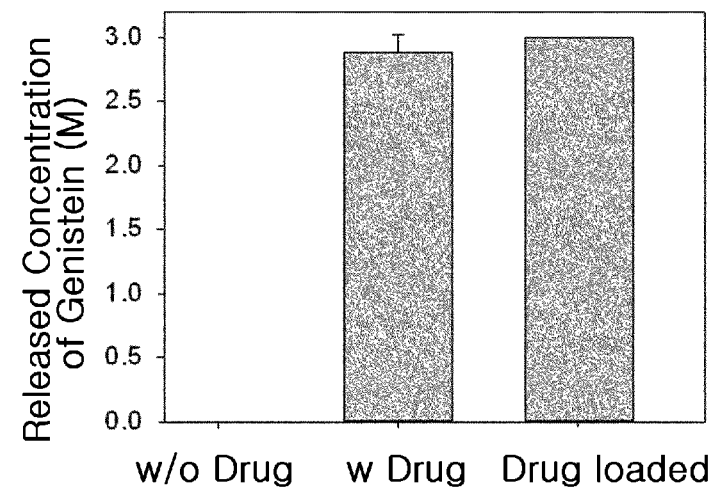

[FIG. 4f]
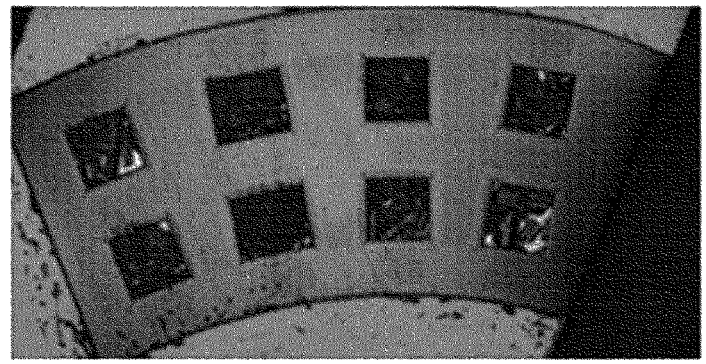
[FIG. 4g]
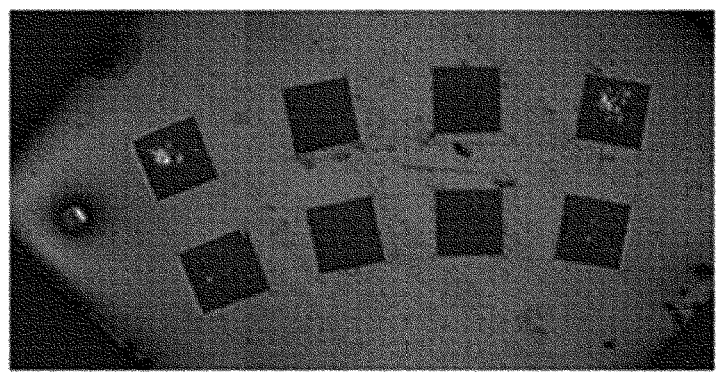
[FIG. 4h]
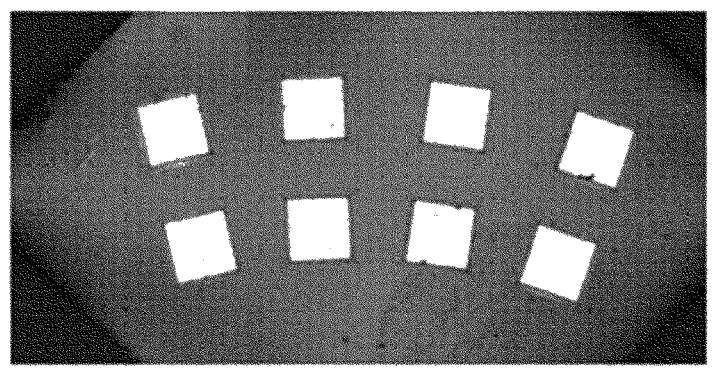

[FIG. 5]
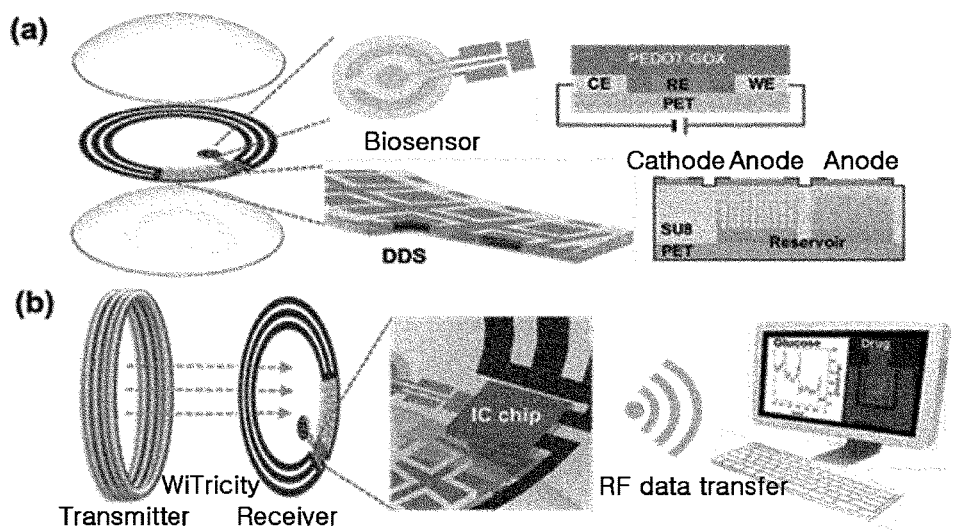

[FIG. 6a]
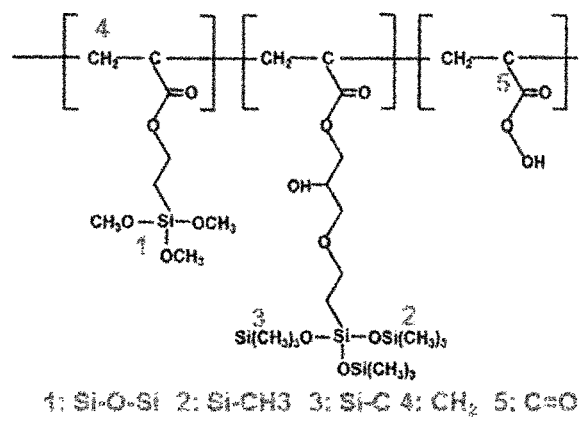
1: Si-O-Si  2: Si-CH3  3: Si-C  4: CH₂  5: C=O
[FIG. 6b]
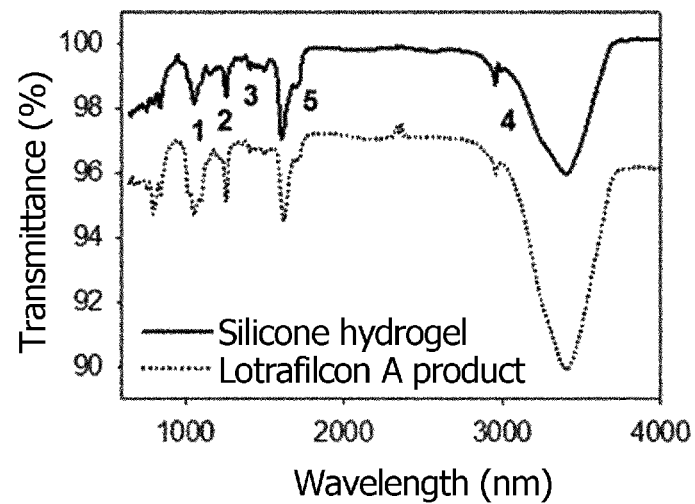

[FIG. 6c]
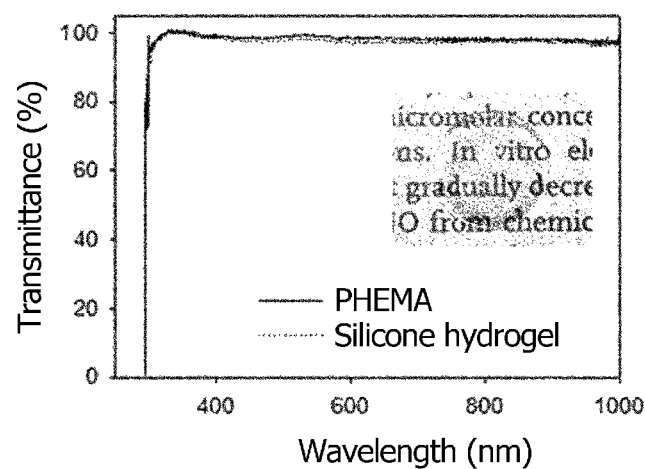
[FIG. 6d]
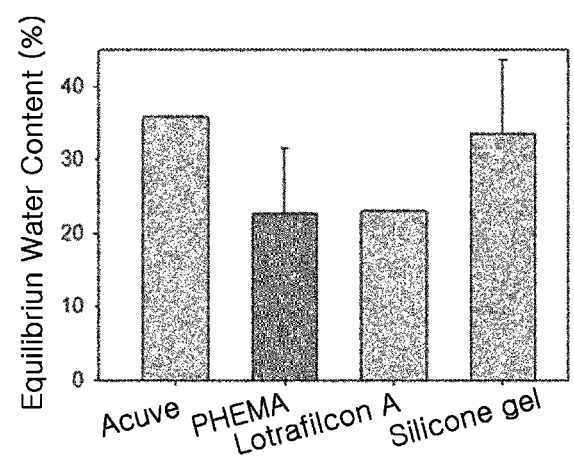

[FIG. 6e]
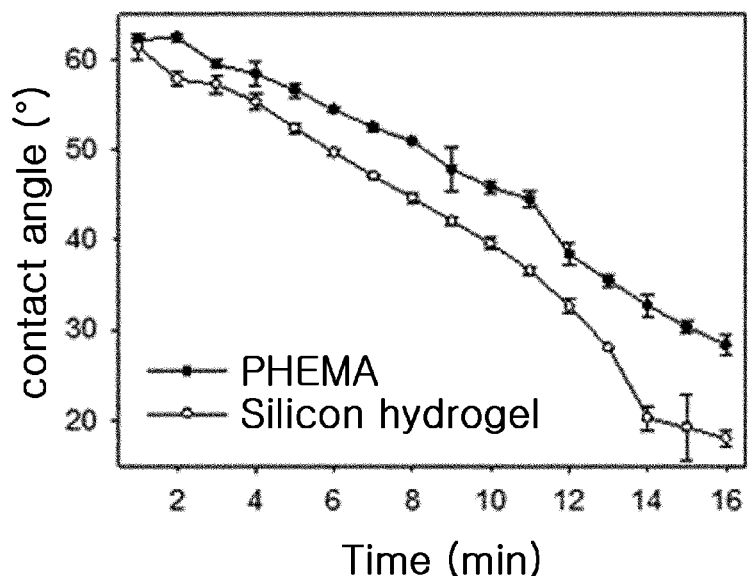
[FIG. 6f]
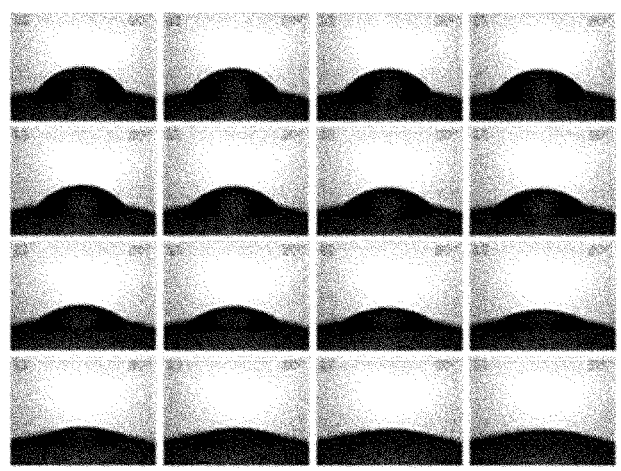

[FIG. 7]
[FIG. 8]
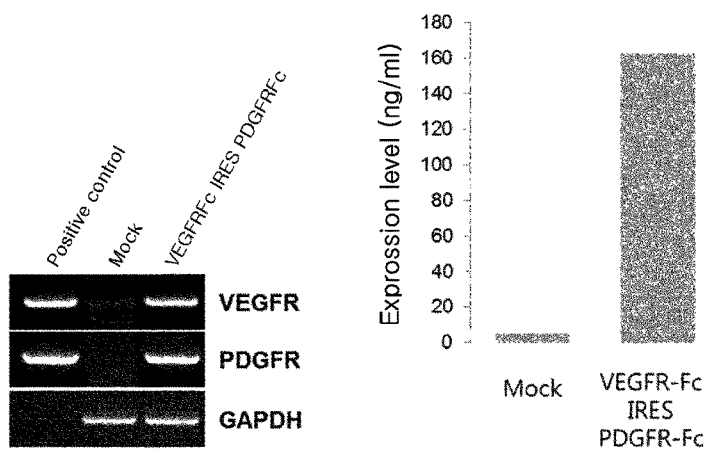
[FIG. 9]
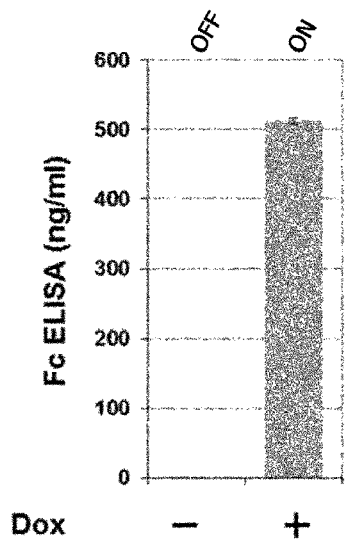

[FIG. 10]
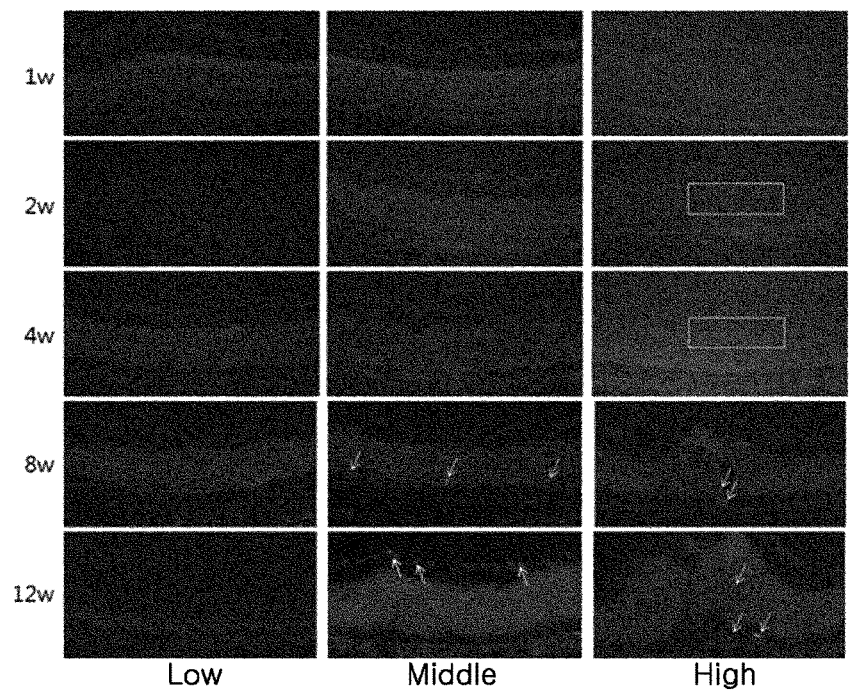
[FIG. 11]
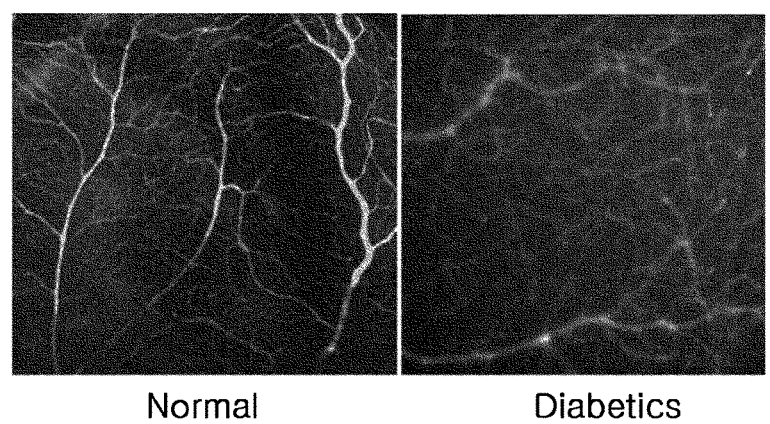

[FIG. 12]
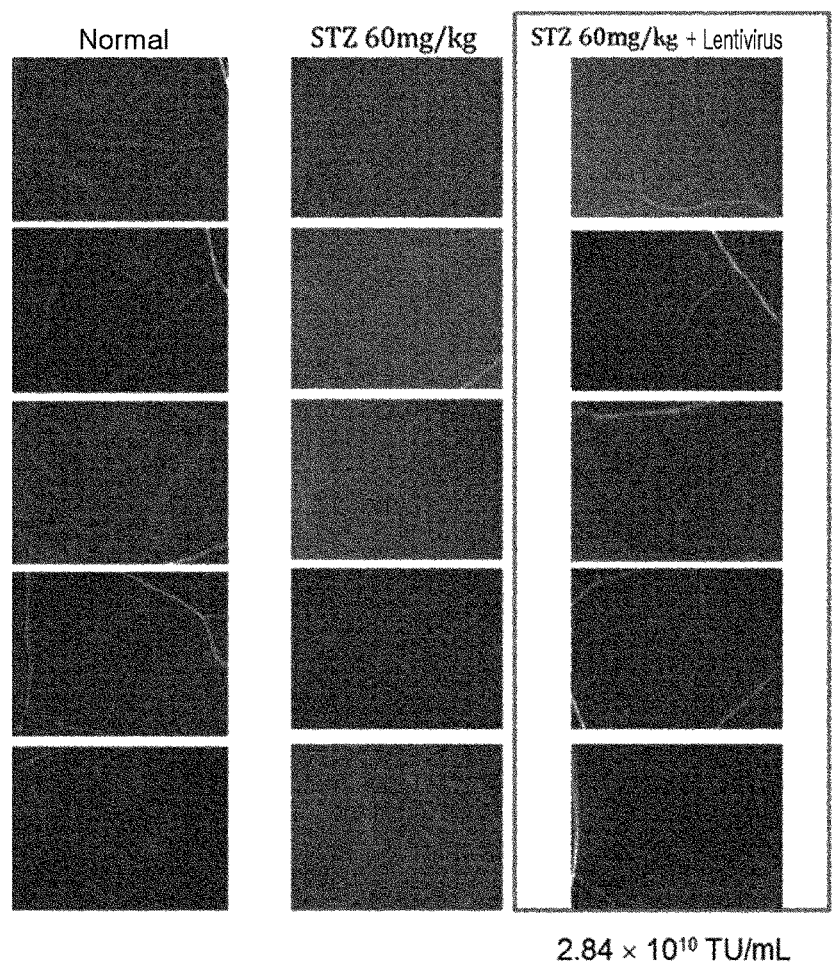
2.84 × 10$^{10}$ TU/mL

[FIG. 13]
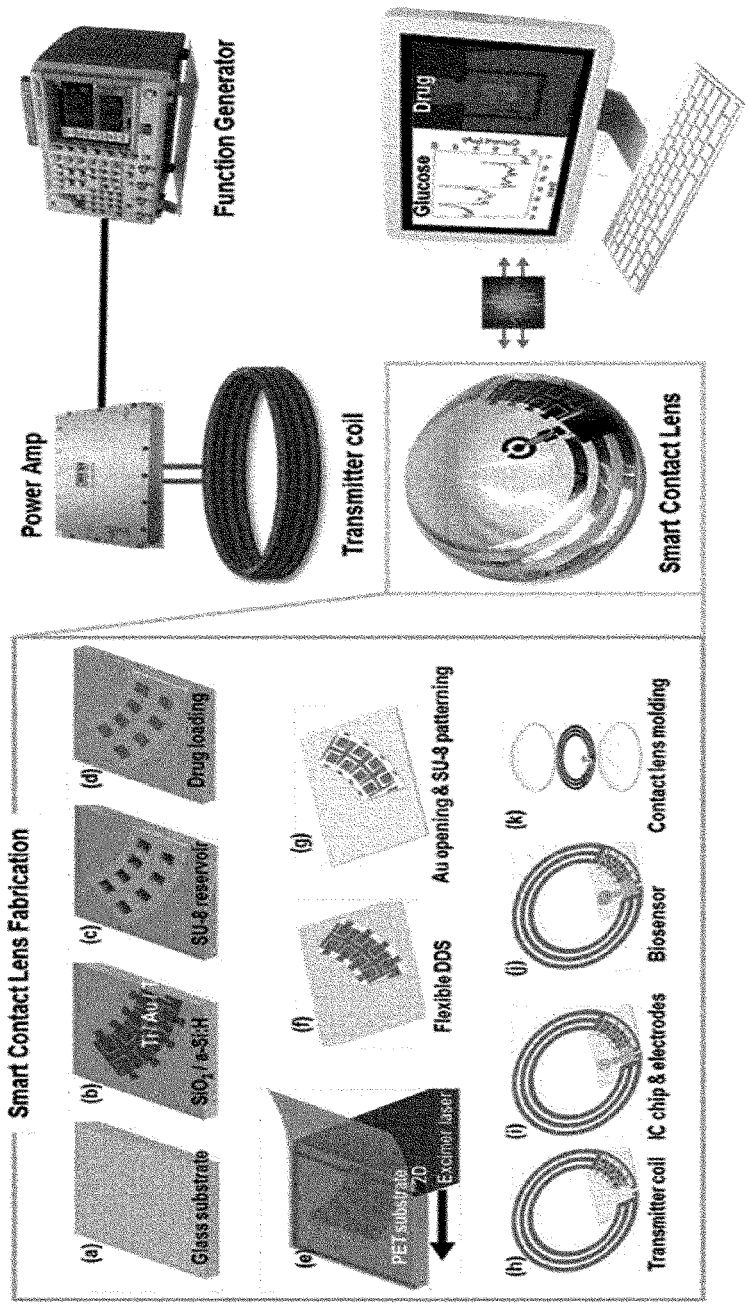

[FIG. 14]
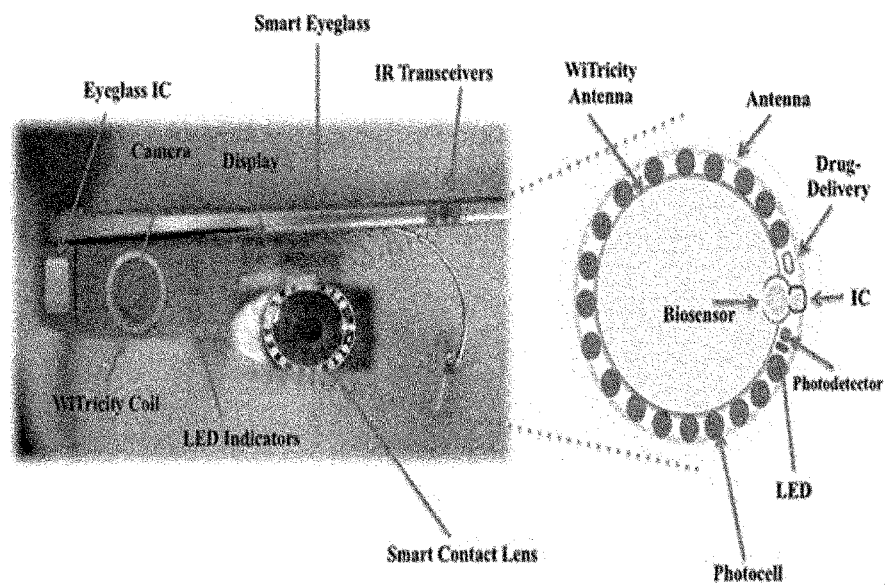
[FIG. 15]
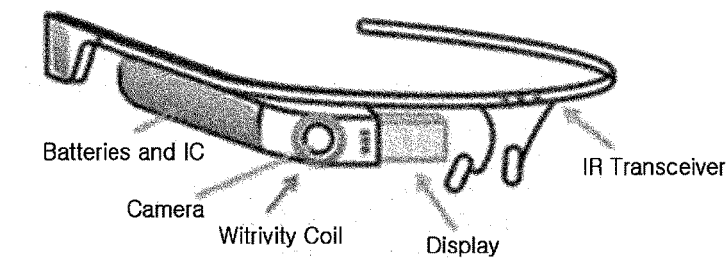
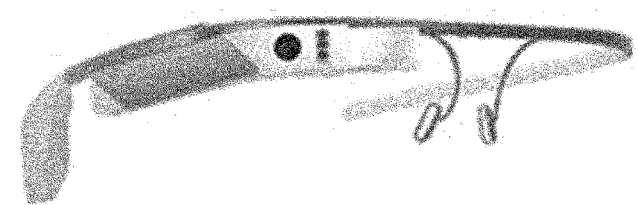

SMART CONTACT LENSES AND SMART GLASSES

TECHNICAL FIELD

The present invention relates to a smart contact lens and smart glasses.

BACKGROUND ART

Research on smart wearable devices that are compact and light to be equipped on a body and have improved convenience is being very actively conducted. Samsung Electronics, Apple, Google, Nike, Adidas and so forth are representative companies that have researched in earnest to launch innovative products.

Google presented a smart watch after Google Glass 2.0, and recently has attracted new attention with the development of a smart contact lens. Likewise, many global research companies are developing a variety of electronic devices to diagnose and treat human diseases, keeping up with the development of e-health systems. Also, for more convenient treatment of a disease and regular injection and drug administration, a diagnosing system capable of simply controlling a drug delivery system using a smartphone has been developed.

Generally, glasses are used for vision correction or eye protection from the sun. Currently-presented special glasses are Google Glass developed by Google-X manufactured by incorporating an electronic device into glasses for real life convenience, Recon Jet developed by Recon, and electronic glasses that are developed by Epson, Lumus, Vuzix, Oakley, Laster, Olympus, Digilens, Microsoft Fortaleza and Sony. Such special glasses can be used to take a photograph or record a video or audio, and show a specific screen. However, such special glasses are too large and heavy to be used for a long time, and thus are inconvenient. The latest special glasses are Google Glass that uses optical head-mounted display (OHMD) technology. While the Google glass is a pair of multi-functional special glasses having various functions, it consumes high power, has a slow display conversion rate and is very expensive, and therefore it is disadvantageous to be used generally.

PATENT DOCUMENTS

1. Korean Unexamined Patent Publication No. 2011-0127658

DISCLOSURE

Technical Problem

Angiogenesis, which is one of the eye diseases, is a serious disease that can cause blindness, and continuously develops without recovery. For this reason, a system for diagnosing a disease in real time regularly and accurately in the body is needed. Therefore, the system requires a sensor that can sense nitrogen monoxide, a vascular endothelial growth factor (VEGF) or glucose, which is excessively secreted from the eye in angiogenesis. However, some of a variety of sensors that have been developed so far, for example, various enzymes, cells, antigens or tissues, have instability in a fluid, show low sensitivity in sensing a target material. Therefore, technology of accurately sensing a target material in a human body fluid is needed.

Also, to administer a drug to the eye in order to treat an eye disease, drug injection using eye drops, intraocular injection or surgery is used. However, in the case of eye drops, there is a limit to an amount of the drug that can be actually injected into the eyes due to the cleansing effect of tears, and thus have very low efficiency. Intraocular injection has high efficiency, but is accompanied with pain. The injection of a drug via surgery has various side effects. For this reason, a drug delivery system for increasing efficiency and minimizing side effects is needed.

Also, for a disease requiring long-term drug release, a drug delivery system using a mobile phone or a PC control is needed to avoid the hassle of regular drug administration. Today, to prevent vision loss caused by macular degeneration, research on inhibiting activity of various factors causing abnormal vascular proliferation, such as VEGF, using genetic therapies has been conducted. However, because of a treatment limitation caused by the instability and low efficiency of a drug, a treating method using a stable viral vector is needed.

Technical Solution

The present invention provides a contact lens, which includes a sensor to which a probe capable of sensing a disease marker is fixed; and a drug reservoir formed in a drug well, which is formed at the inner side of the contact lens in contact with the eye to be indented toward the outer side thereof and sealed by an electrode pattern containing gold.

Here, when the disease marker is sensed by the sensor, the gold of the electrode pattern of the drug reservoir is dissolved in chlorine of the body, resulting in $AuCl_4^-$, and thus the drug reservoir is opened.

Also, the present invention provides a method for producing a contact lens including a sensor to which a probe capable of sensing a disease marker is fixed; and a drug reservoir.

Here, the drug reservoir is produced by (a) forming a buffer layer on an amorphous silicon layer which is formed on one surface of a transparent substrate, and forming an electrode pattern containing gold on a partial surface of the buffer layer;

(b) forming a drug well layer including a drug well for accommodating a drug on the buffer layer on which the electrode pattern is not formed and the electrode pattern;

(c) stacking a plastic substrate on the drug well layer; and (d) separating the amorphous silicon layer by applying a laser beam to the surface of the transparent substrate on which the amorphous silicon layer is not formed.

Also, the present invention provides a system, which includes a smart contact lens including a sensor to which a probe capable of sensing a disease marker is fixed and a drug reservoir; and smart glasses for transmitting electrical signals wirelessly to control operation of the sensor and the drug reservoir of the smart contact lens.

Advantageous Effects

According to the present invention, a sensor in a contact lens can sense a disease in real time, and therefore the progression of a patient's disease can be easily and rapidly identified. Also, the sensor can be used in a fluid for a long time due to high stability, and more accurately determine whether the disease can be treated or not treated due to high sensitivity.

Also, technology of sensing a disease marker in the eye such as nitrogen monoxide (NO), VEGF or glucose using a sensor can be applied to various cancer diagnosing systems.

A drug reservoir inserted into a contact lens can be electrically controlled to release a drug at a desired time, and thus can be applied to treat a variety of eye diseases.

Aflibercept expressed by a lentivirus, which is inserted into the drug reservoir, is a stable and highly-effective drug for ocular angiogenesis.

By using a drug reservoir-based drug delivery system capable of being controlled by electrical signals, for example, tetracycline may be released at a desired time, and the system that is turned on or off by the tetracycline can generate a drug in cells. Accordingly, the system can be used in treatment of eye diseases.

Also, in the present invention, a protein expression-based advanced therapeutic gene introduction method, which has higher biological activity and sustaining power in the body than conventional antibody therapies and prevents apoptosis induced by ADCC and CDC responses can be constructed by introducing hybrid Fc utilizing the characteristics of immunoglobulins present in the body to a therapeutic substance. Therefore, a gene transfer system using an animal trial approximating a clinical trial and a nano system can be produced.

DESCRIPTION OF DRAWINGS

FIG. 1 shows (a) an image of the structure of a glucose sensor, (b) a graph of real-time current variations in the glucose sensor according to glucose concentrations, and (c) a graph of current variations in the glucose sensor with respect to substances, other than glucose.

FIG. 2 shows (a) a front view, (b) a schematic cross-sectional view and (c) an SEM image of a drug reservoir.

FIG. 3 shows a method for measuring an operating current for a drug reservoir produced on a flexible substrate and its result.

FIG. 4 shows (a) images of drug reservoirs before and after drug release, (b) fluorescent images of emission of a fluorescent dye, (c to e) graphs of current variations and concentrations of a released drug over time, and (f to h) images of drug reservoirs in which either and none of metformin and genistein are loaded, respectively.

FIG. 5 is a diagram showing the structure and a signal transmitting and receiving process of a smart contact lens.

FIG. 6 shows the results of evaluation of the characteristics of a contact lens.

FIG. 7 is an image of an expression system of a lentivirus for regulating expression of an anti-angiogenic factor by tetracycline.

FIG. 8 shows expression of a therapeutic gene in cells infected by a lentivirus in mRNA and protein levels.

FIG. 9 shows a graph showing expression of VEGFR-Fc and PDGFR-Fc according to the presence or absence of DOx.

FIG. 10 shows intraocular expression of a lentivirus expressing GFP in animal models.

FIG. 11 shows that a diabetic retinopathy animal model is constructed using STZ.

FIG. 12 shows that a lentivirus expressing VEGFR-Fc and PDGFR-Fc has an inhibitory effect on intraocular angiogenesis in diabetic retinopathy animal models.

FIG. 13 shows a diagram illustrating a process of producing a contact lens and energy supply and wireless communication using WiTricity.

FIG. 14 shows images of a contact lens and smart glasses.

FIG. 15 shows an outline image of smart glasses.

MODES OF THE INVENTION

The present invention provides a contact lens, which includes a sensor to which a probe capable of sensing a disease marker is fixed; and a drug reservoir formed in a form of a drug well, which is formed at the inner side of the contact lens in contact with the eye to be indented toward the outer side thereof and sealed by an electrode pattern containing gold.

When the disease marker is sensed by the sensor, the gold of the electrode pattern of the drug reservoir is dissolved in chlorine of the body, resulting in $AuCl_4^-$, and thus the drug reservoir is opened.

In the present invention, the contact lens may be based on a polymer such as a silicone hydrogel, poly(2-hydroxyethylmethacrylate) (PHEMA), poly(methyl methacrylate) (PMMA), poly(lactic-co-glycolic acid) (PLGA), polyvinylpyrrolidone (PVP) or polyvinylacetate (PVA). In detail, the contact lens may be based on a silicone hydrogel or PHEMA.

The contact lens according to the present invention includes the sensor and the drug reservoir.

In the present invention, the sensor has a fixed probe capable of sensing a disease marker, and the probe determines the presence or absence of a disease by sensing the disease marker.

A type of the disease marker is not particularly limited, and the disease marker may be one or more selected from the group consisting of nitrogen monoxide (NO), VEGF, an epidermal growth factor (EGF), glucose, lactose, a water content, flavin adenine dinucleotide (FAD), Bandeiraea simplicifolia agglutinin (BSA), hydrogen peroxide, oxygen, ascorbate, lysozyme, iron, lactoferrin, a phospholipid, an osmotic pressure and an intraocular pressure, and specifically, NO, VEGF or glucose.

Also, a type of the probe is not particularly limited, and the probe may be one or more selected from the group consisting of hemin, an aptamer, glucose oxidase, an antigen, an antibody, RNA and DNA, and specifically, hemin, an aptamer or glucose oxidase.

In the present invention, the sensor may sense a current change occurring when the disease marker binds to the probe, and thereby determine the presence or absence of a disease.

In one exemplary embodiment, the sensor may be an NO sensor, a VEGF sensor or a glucose sensor.

In the present invention, the NO sensor, the VEGF sensor or the glucose sensor may accurately sense a disease from the body fluid of a human.

The NO sensor may be produced by bonding a hemin molecule to a poly(3,4-ethylenedioxythiophene) (PEDOT) channel-based sensor selectively capturing NO. The sensor has high stability due to pi ($\pi$-$\pi$) electron bonds between the PEDOT and the hemin molecule, and may sense NO in a fluid in real time with high sensitivity due to a high binding affinity of hemin to NO.

Also, the VEGF sensor has high sensitivity and accuracy since it uses a nanowire semiconductor and a carbon nanotube-based transistor, and is able to immediately sense VEGF. Specifically, the VEGF sensor has an anti-VEGF aptamer binding to gates of n-type and p-type carbon nanotube transistors, and thus may sense VEGF when a VEGF molecule binds to the aptamer.

In one exemplary embodiment, the above-described sensors are linked to an application-specific integrated circuit (ASIC) chip to enable wireless communication. The sensor may be operated by sensing (receiving) electrical signals transmitted from smart glasses that will be described below via the ASIC chip, and may transmit a sensed result to the smart glasses to allow the smart glasses to control operation of the drug reservoir.

In the present invention, the drug reservoir may be formed in a form of a drug well. The drug well may be formed at an inner side of the contact lens that is in contact with the eye to be indented toward the outer side thereof, and may be sealed by an electrode pattern containing gold.

In one exemplary embodiment, the drug reservoir may include a drug or a drug carrier capable of releasing a drug, and a drug releasing control substance.

Here, the drug may be a protein drug, and the drug carrier may be a viral vector expressing the protein drug.

A type of the viral vector is not particularly limited, and the viral vector may be one or more selected from the group consisting of a lentivirus vector, a retrovirus vector, a baculovirus vector, a parvovirus vector, a Semliki Forest virus vector, a canarypox virus vector, a vaccinia virus vector, a fowlpox virus vector, a sindbis virus vector, an adenovirus vector, a piconavirus vector and an alphavirus vector. Specifically, the viral vector may be lentivirus vector.

In one exemplary embodiment, the viral vector may be a recombinant virus produced by a recombinant vector. The recombinant virus may include a DNA cassette having one or more nucleic acid sequences encoding protein drugs. Here, the protein drugs may be VEGFR and PDGFR, and may be Fc-binding fusion proteins.

That is, the DNA cassette may include a nucleic acid sequence encoding VEGFR-Fc and a nucleic acid sequence encoding PDGFR-Fc, which are placed between and linked to transcription/translation initiation nucleic acid sequences.

The transcription/translation initiation nucleic acid sequences may be internal ribosome entry site (IRES) nucleic acid sequences.

The term "internal ribosome entry site (IRES)" used herein refers to a specific region present in mRNA to which a ribosome directly binds to enable synthesis of a variety of proteins from one mRNA in eukaryotic cells.

In one exemplary embodiment, expression of the inserted gene may be controlled by tetracycline or doxycycline in the DNA cassette.

In the drug reservoir according to the present invention, the electrode pattern may contain gold. Specifically, the electrode pattern may be a positive electrode, and have a configuration of Ti/Au/Ti.

When the drug reservoir of the present invention senses (receives) electrical signals transmitted from smart glasses that will be described below, the gold of the electrode pattern is dissolved in chlorine, resulting in $AuCl_4^-$, and thus the electrode pattern is opened, and a drug in the drug reservoir may be released to the outside.

Also, the present invention provides a method for producing a contact lens including a sensor to which a probe capable of sensing a disease marker is fixed; and a drug reservoir.

The drug reservoir may be produced by (a) forming a buffer layer on an amorphous silicon layer which is formed on one surface of a transparent substrate, and forming an electrode pattern containing gold on a partial surface of the buffer layer;

(b) forming a drug well layer including a drug well for accommodating a drug on the buffer layer on which the electrode pattern is not formed and the electrode pattern;

(c) stacking a plastic substrate on the drug well layer; and (d) separating the amorphous silicon layer by applying a laser beam to the surface of the transparent substrate on which the amorphous silicon layer is not formed.

In the step (a), the electrode pattern is formed on a buffer layer of the structure in which a transparent substrate, an amorphous silicon layer and the buffer layer are sequentially formed.

In one exemplary embodiment, a type of the transparent substrate is not particularly limited as long it is penetrable by a laser beam, and the transparent substrate may be glass or sapphire. The amorphous silicon layer may be a hydrogen-containing amorphous silicon layer (a-Si:H). When a laser beam is applied onto the transparent substrate and the amorphous silicon layer, hydrogen in the amorphous silicon layer is vaporized, and the amorphous silicon layer may be characterized as being separated from the transparent substrate.

A type of the buffer layer formed on the amorphous silicon layer is not particularly limited as long as it can block heat and pressure generated by the laser beam, and the buffer layer may include, for example, silicon dioxide ($SiO_2$). In the application of a laser beam through a transparent substrate that will be described below, the laser beam may not pass through the buffer layer, optical energy of the laser beam may be converted into thermal energy, and thus hydrogen in the amorphous silicon layer may be vaporized.

In one exemplary embodiment, the electrode pattern stacked on the buffer layer may consist of a square-shaped positive electrode and a negative electrode connected in common to the positive electrode, and have an array of a plurality of positive electrodes. The positive electrode of the electrode pattern may contain gold, and specifically, formed of Ti/Au/Ti. The gold of the electrode pattern may be removed through electrolysis by a voltage supplied in an electrolyte. Accordingly, the positive electrode of the electrode pattern may be used as a gate for a pathway delivering an accommodated drug by a voltage. The electrode pattern may be formed on a partial surface of the buffer layer.

In the present invention, in the step (b), a drug well layer having a drug well for accommodating a drug is formed on the buffer layer on which the electrode pattern is not formed and the electrode pattern.

In one exemplary embodiment, the drug well layer may include SU8 (or SU-8). The SU8 may be a negative epoxy-type near-UV photoresist.

In this step, after SU8 is formed on the buffer layer not having an electrode pattern and the electrode pattern, the SU8 may be patterned, thereby forming a drug well having an opening. Here, the opening of the drug well may be formed on the electrode pattern, and specifically, a positive electrode pattern, and the positive electrode of the underlying electrode pattern may be exposed through the opening. A size of the drug well (reservoir) may be easily controlled according to a concentration of SU8, a spin-coating condition, and a size of a patterning mask.

In the present invention, in the step (c), a plastic substrate is stacked on the drug well layer. In this step, a flexible plastic substrate coated with an adhesive layer is stacked on the drug well layer to seal the drug well. Instead of the coated adhesive layer, an adhesive tape may also be used for adhesion of the plastic substrate to the drug well layer.

In the present invention, in the step (d), the amorphous silicon layer is separated by applying a laser beam to one surface of the transparent substrate not having the amorphous silicon layer. In this step, as hydrogen contained in the amorphous silicon layer is vaporized by the laser beam, and a pressure applied to the amorphous silicon layer increases, the amorphous silicon layer and the transparent substrate may be physically and chemically separated from each other.

In one exemplary embodiment, after the step (d), a step of patterning the buffer layer to expose the electrode pattern in contact with the drug well may be further performed.

Alternatively, in one exemplary embodiment, after the step (d), a step of depositing an SU8 layer on the drug well layer and patterning the SU8 layer and the buffer layer to expose the electrode pattern in contact with the drug well may be further performed.

When the electrode pattern is exposed by patterning the buffer layer, the electrode pattern may be partially exposed.

Also, before the buffer layer is patterned, an electrode layer may be further formed by depositing a biocompatible metal, for example, gold (Au), and may be patterned in a window shape, and then the buffer layer may be patterned to expose the electrode pattern (positive electrode). This is to operate the electrode layer with low power by forming a supporting layer on the buffer layer due to the very thin positive electrode, and by reducing the size and a distance between the negative electrode and the positive electrode to a minimal level due to the three-dimensional structure.

When the produced drug reservoir is inserted into the body, and a voltage is applied between the positive electrode and the negative electrode, the positive electrode of the electrode pattern is dissolved in chlorine of PBS, thereby producing $AuCl_4^-$, and thus the electrode pattern (positive electrode) may be perforated, and the drug enclosed in the reservoir may be released.

Also, the present invention provides a system, which includes a smart contact lens including a sensor to which a probe capable of sensing a disease marker is fixed and a drug reservoir; and smart glasses for transmitting electrical signals wirelessly to control operation of the sensor and the drug reservoir of the smart contact lens.

The present invention may provide smart glasses enabling micro-unit long distance control using a state-of-the-art nano material and on-chip optoelectronics, a complementary metal-oxide-semiconductor (CMOS), a flexible and very bio-friendly micro electro-mechanical system (MEMS), and nano electro-mechanical system (NEMS) technology.

For the smart glasses, electrical power may be implemented using hybrid auto powering (miniaturized photovoltaic system for power harvesting) and wireless inductive power transfer (WiTricity) technology, and wireless communication may be performed using Bluetooth, infra-red (IR) and radio frequency (RF) in the smart glasses.

The smart glasses use android OS as an operating system, and may be equipped with an OMAP 4430 SoC, a dual-core CPU and a 4 GB RAM memory. A display with 640×360 pixels may be used, and a Bone conduction transducer may be used for an audio. In the smart glasses, an optical sensor, a biosensor, a pressure, a temperature, and functions of an acoustic EM sensor may be controlled via a voice through a microphone, and the smart glasses may be paired with a smartphone, a smart watch or PC. An internal 100 mAh lithium ion battery may be used as power, and a photocell may be inserted for auto powering. A total weight may be less than 20 g, and Wi-Fi 802.11b/g, Bluetooth and micro USB may be used for connectivity. Photos: >15 MP; Videos: >720p may be implemented using a mounted camera.

Also, in the smart contact lens, the sensor and the drug reservoir may be operated using an ASIC chip, and energy may be provided using WiTricity and a photodetector. Power control may be performed by suitably controlling a voltage and time using a power management integrated circuit (PMIC).

In one exemplary embodiment, the sensor may be operated by an electrical signal transmitted from the smart glasses, and the sensor receiving the signal may sense a current change, which occurs when the disease marker binds to the probe, and then transmit the sensed result to the smart glasses through RF wireless communication.

Also, in one exemplary embodiment, the drug reservoir may be operated by an electrical signal transmitted from the smart glasses, and in the drug reservoir receiving the signal, the gold of the electrode pattern sealing the drug reservoir may be dissolved in chlorine, resulting in $AuCl_4^-$, and thus the electrode pattern may be opened.

Power generated from a WiTricity coil of the smart glasses may be received at a WiTricity antenna of the smart contact lens, and power received through IC chip control may be used to operate the sensor and/or the drug reservoir.

Also, the smart contact lens may further include a photodetector converting sensed external light into electricity and a photocell for auto powering, and power produced thereby may be used to operate the sensor and/or the drug reservoir.

EXAMPLES

Hereinafter, the present invention will be described in detail with reference to the following examples. However, the following examples are merely provided to explain the present invention, but the scope of the present invention is not limited to the examples.

Preparation Example 1. Production of Sensor: Production of Glucose Sensor

Three electrodes including a working electrode (WE), a reference electrode (RE) and a counter electrode (CE) were deposited on a polyethylene terephthalate (PET) substrate having a thickness of 25 μm using a shadow mask. A conductive electrode consisting of 20 nm titanium (Ti), 10 nm palladium (Pd) and 200 nm platinum (Pt) was deposited using an e-beam metal evaporator. Additionally, the RE was coated with 200 nm silver (Ag) using Ag/AgCl ink and a shadow mask.

In addition, glucose oxidase (GOX) was mixed with a poly(3,4-ethylenedioxythiophene)-polystyrene sulfonate (PEDOT-PSS) 1000 solution to have a concentration of 20 mg·mL$^{-1}$, and then 2 μl of the solution was applied to coat the electrode and hardened in a titanium isopropoxide vapor environment.

In the present invention, FIG. 1(a) is an image of the glucose sensor produced according to the present invention.

Experimental Example 1. Reactions of Sensor

For the above-described glucose sensor produced in Preparation Example 1, variations in current over time according to the concentration of glucose and variations in current with respect to different materials, other than glucose, were measured.

To measure the variations in current according to glucose concentration, the glucose sensor was connected with a probe station, 700 mV was supplied, glucose was added in a variety of concentrations of 0, 0.25, 0.5, 1, 2 and 4 mM, and then the current variations were observed.

The resultant current variations are shown in FIG. 1. FIG. 1(b) is a graph showing the result of measuring the current variations of the glucose sensor over time according to glucose concentration, and FIG. 1(c) is a graph showing the result of measuring the current variations of the glucose sensor with respect to materials, other than glucose.

As shown in FIG. 1, it can be seen that an increase in current was directly proportional to the glucose concentration, and there were no current variations with respect to materials (BSA, ovalbumin, Fe, NaCl, lysozyme, lipocalin and KCl), other than glucose.

Preparation Example 2. Production of Gold-Deposited Drug Reservoir

A gold-deposited drug reservoir was produced by the method as follows.

The drug reservoir was produced by the method illustrated with reference to FIGS. 13(a) to (g).

First, a glass substrate was prepared (FIG. 13(a)), a hydrogen-containing amorphous silicon layer (a-Si:H) was deposited on the glass substrate, a buffer layer (silicon dioxide, $SiO_2$) was stacked on the amorphous silicon layer, and an electrode pattern was stacked on a partial surface of the buffer layer (FIG. 13(b)). For the electrode pattern, a plurality of positive electrodes may be formed in an array, and a negative electrode may be formed in a window shape. The positive electrodes of the electrode pattern may contain gold, and specifically, Ti/Au/Ti.

Afterward, a drug well layer (SU-8) was formed on the buffer layer not having the electrode pattern and the electrode pattern and patterned, thereby forming a drug well having an opening. The patterning was performed on the drug well layer formed on the electrode pattern, and the positive electrode of the electrode pattern was exposed through the opening (FIG. 13(c)).

A drug was loaded in the drug well layer (FIG. 13(d)), and a flexible plastic substrate (PET) coated with an adhesive layer was formed on the drug well layer to seal the drug well.

Afterward, a laser lift-off process for applying a laser beam to the back side of the glass substrate was performed (FIGS. 13(e)-(f)). Accordingly, the hydrogen contained in the amorphous silicon layer was vaporized and a pressure was increased in the amorphous silicon layer, and therefore the glass substrate and the amorphous silicon layer were separated from the buffer layer.

Subsequently, the buffer layer was patterned and etched to expose some of the negative electrode and/or the positive electrodes, resulting in connection of the electrode to the outside (FIG. 13(g)).

Alternatively, in the present invention, before the buffer layer was patterned, SU-8 may be further stacked, and then etched to expose the electrode pattern (positive electrode).

In the present invention, FIG. 2 shows (a) a front view, (b) a schematic cross-sectional view and (c) an SEM image of a drug reservoir produced according to the present invention. In FIG. 2(c), SU8-50 and SU8-5 indicate that the SU8 has respective thicknesses of 50 μm and 5 μm.

As shown in FIG. 2(a), a drug reservoir storing drugs which are stored separately in a plurality of spaces may be produced by a method according to the present invention.

Also, according to the structures of FIGS. 2(b) and 2(c), when voltage is applied between the positive electrode and the negative electrode of the drug reservoir, the positive electrode of the electrode pattern is dissolved in chloride of PBS, resulting in $AuCl_4^-$, and the positive electrode is perforated and thus the drug enclosed in the reservoir may be released. Accordingly, an MEMS-based drug delivery system may be realized.

Experimental Example 2. Drug Release from Drug Reservoir by Electrical Signal

The above-described drug reservoir produced in Preparation Example 2 was added to a 1.0 mM PBS buffer solution with pH 7.4, and a voltage of 1.8 V was applied to the positive electrode and the negative electrode for 5 seconds.

In the present invention, FIG. 3 shows the result of measuring current variations of the drug reservoir.

In detail, FIG. 3(a) shows the drug reservoir, which is attached to a cylinder to measure a current required for operating the drug reservoir when bending the drug reservoir, FIG. 3(b) shows a bending radius measured after the drug reservoir is placed on the cylinder, FIG. 3(c) is a graph showing the result of measuring a current required for drug release as the drug reservoir is bent, and FIG. 3(d) is an image of the drug reservoir placed on a polydimethylsiloxane (PDMS) hemisphere with the radius of curvature of 5, 10, 15, 20, or 25 mm.

As shown in FIG. 3, it can be seen that the drug is released from the drug reservoir under a uniform current regardless of bending.

Also, in the present invention, FIG. 4 shows (a) images before and after the drug is released from the drug reservoir, (b) a fluorescent image of emission of a fluorescent dye, (c) a graph of current variation over time, (d-e) graphs of concentrations of a released drug, and (f-h) images of the drug reservoir in which either or none of metformin and genistein is loaded, respectively.

First, FIG. 4(a) shows images before (left) and after (right) a drug is released from the drug reservoir in response to an electrical signal. According to FIG. 4(a), it can be seen that a drug is released from the drug reservoir in response to an electrical signal, and fluorescence is generated.

FIG. 4(b) shows fluorescence images obtained before (left) and after (right) a drug is released from the drug reservoir in response to an electrical signal. A red dye-added drug was used, and according to FIG. 4(b), it can be seen that the drug is released from the drug reservoir in response to an electrical signal, and fluorescence is generated.

FIG. 4(c) is a graph showing current variation over time, and FIGS. 4(d) and (e) are graphs showing concentrations of released drugs, for example, in the present invention, each of metformin and genistein was added to the drug reservoir, and then its release concentration was measured. In FIGS. 4(d) and (e), contents of the drugs released from the drug reservoir without a drug, and the drug reservoir with a drug were compared with the initially loaded content of a drug. It can be seen from the graphs that, once electrical signals are applied five times, a gold film sealing the drug reservoir is dissolved, and then an approximately 3 M drug is released.

In addition, FIGS. 4(f) to (h) are images of the drug reservoirs with either of metformin and genistein, and the drug reservoir without a drug, and it can be seen from the graphs that, while the concentration of a released drug in the reservoir without a drug is 0, in the reservoir with a drug, a drug is released at an amount similar to the initially loaded amount.

Preparation Example 3. Production of Content Lens

A contact lens was produced using a material with silicone.

First, 1 mL of methacryloxypropyl-tris(trimethylsiloxy) silane was mixed with 0.62 mL of N,N-dimethyl acrylamide (DMA), 1 mL of methacryloxypropyl (MC)-PDMS macromere, 0.3 mL of methyl acrylic acid (MAA), 0.1 mL of ethanol, and 0.2 mL of N-vinylpyrrolidone (NVP) under a nitrogen environment for 15 minutes. In addition, 12 μg of an ultraviolet (UV) initiator, TPO, was added and mixed with the resultant solution for 5 minutes, thereby preparing a "solution 1."

As a control, without using silicone, 1 mL of poly (hydroxyethylmethacrylate) (PHEMA) and 25 μl of a cross-linking agent, ethylene glycol dimethacrylate (EGDMA) were mixed with 12 μg of TPO, thereby preparing a "solution 2."

After 0.2 mL each of the prepared solution 1 and solution 2 were subjected to radical polymerization in a specially-designed polypropylene (PP) mold, a surface of the polymer became hydrophilic due to ozone plasma, and then stored in a PBS solution.

Afterward, the glucose sensor produced in Preparation Example 1 was connected to an ASIC chip to enable wireless communication, the chip-connected sensor and the drug reservoir produced in Preparation Example 2 were added to the PBS solution, and subjected to radical polymerization in a PP mold, thereby producing a lens.

In the present invention, FIG. 5 is an image showing the structure and the signal transmitting and receiving process of a smart contact lens.

As shown in FIG. 5, the contact lens has a sensor and a drug reservoir (DDS) (refer to FIG. 5(a)).

Also, the produced contact lens enables wireless communication via a chip connected to the sensor in the lens (refer to FIG. 5(b)).

Experimental Example 3. Characteristics of Contact Lens

The characteristics of the contact lens produced in Preparation Example 3 was evaluated.

The evaluation results are shown in FIG. 6. In FIG. 6, a silicone hydrogel refers to a lens produced using the solution 1 in Preparation Example 3, and PHEMA refers to a lens produced using the solution 2. PHEMA is a commercial lens, and Lotrafilcon A is a commercial silicone lens.

FIG. 6(a) shows the structure of the silicone hydrogel. Referring to FIG. 6(a), it can be seen that added monomers are suitably polymerized.

FIG. 6(b) is a graph of analyzing a molecular structure of the lens. The molecular structure was analyzed using attenuated total reflectance-Fourier transform infrared spectroscopy (ATR-FTIR) (TENSOR 27, Bruker).

FIG. 6(c) is a graph showing transmittance of the lens in a visible region. The transmittance was measured using a Vis spectrometer (SCINCO), and the transparency of the lens in the visible region may be identified through the measurement result.

It can be confirmed that the silicone hydrogel and the PHEMA, which are prepared according to the methods of the present invention, exhibit a transmittance close to approximately 100% in a wavelength range of 400 to 1000 nm.

FIG. 6(d) is a graph showing equilibrium water content per lens. The equilibrium water content was calculated by controlling a dry lens weight ($W_{dry}$) and a wet lens weight ($W_{wet}$), through the following equation.

$$(W_{wet} - W_{dry})/W_{dry} \times 100 \qquad \text{<Equation 1>}$$

As shown in FIG. 6(d), it can be confirmed that the silicone hydrogel prepared by the method according to the present invention has a higher water content than other lenses.

Also, FIGS. 6(e) and 6(f) are a graph and an image showing variations in a contact angle over time. The contact angle was measured using SmartDrop (FEMTOFAB). In detail, FIG. 6(e) shows the result of measuring the variations in the contact angle of the silicone hydrogel and PHEMA, and FIG. 6(f) is an image showing the variations in the contact angle of the silicone hydrogel, which are observed by points (hourly) for 16 hours.

As shown in FIGS. 6(e) and 6(f), it can be seen that the lenses tend to be decreased in the contact angle value over time, but the silicone hydrogel prepared by the method according to the present invention has a relatively higher contact angle than other lenses.

Preparation Example 4. Gene Regulation-Based Drug Delivery System

A gene regulation-based drug delivery system was introduced to develop a therapeutic agent for inhibiting a major angiogenesis inducing factor that induces angiogenesis.

To treat ocular angiogenesis, a lentivirus by which an anti-angiogenic drug, aflibercept (VEGF-trap), and a platelet-derived growth factor receptor (PDGFR) were simultaneously expressed was produced.

The aflibercept is an Fc fusion protein, in which amino acid sequences of the second domain (Flt1) of VEGFR1 and the third domain (Flk1) of VEGFR2 are fused to the IgG1 Fc domain, and disclosed in U.S. Pat. No. 7,070,959.

When a platelet-derived growth factor receptor (PDGFR) is expressed with aflibercept, formation of pericytes may be more effectively inhibited. The PDGFR according to the present invention may be formed by fusion of the amino acid sequences of the first, second and third domains of PDGFR. PDGFR may be applied in the case of advanced blood vessel lesions such as the disappearance of blood vessels or angiogenesis, and bleeding, and like aflibercept, may be expressed in the IgG1 Fc domain-fused form.

Here, the IgG1 Fc region fused with the VEGFR protein and the PDGFR protein may be substituted by the Fc region of a modified immunoglobulin, hybrid Fc. Here, the Fc region of the modified immunoglobulin may have weak antibody-dependent cytotoxicity (ADCC) or complement-dependent cytotoxicity (CDC) by modifying the binding affinity between an Fc receptor and a complement. The modification may be accomplished by substitution or deletion of the sequence of the Fc-binding receptor through genetic mutations. Also, the IgG1 Fc region may be expressed by fusion of modified IgG4 according to the known art. The modification may be achieved by mixing the sequences of different types of immunoglobulins.

The term "hybrid Fc" used herein refers to those produced by combining different types of Fc regions. The hybrid Fc may include a human IgD hinge region, and amino acid residues of human IgD CH2 domain, and CH2 and CH3 domains of human IgG4. The hybrid Fc region according to the present invention is disclosed in U.S. Pat. No. 7,867,491, and serves to help in continuous and stable expression of a protein drug.

To produce a lentivirus capable of expressing both of the VEGFR-Fc protein and the PDGFR-Fc protein, a DNA cassette as shown in FIG. 7 was prepared.

Here, a DNA cassette was prepared by placing an IRES between nucleic acid sequences encoding the VEGFR-Fc and PDGFR-Fc proteins to simultaneously express VEGFR-Fc and PDGFR-Fc, and the expression of the VEGFR-R-Fc and PDGFR-Fc was regulated via an on/off system of tetracycline. Here, a Tet-On advanced system was used, and in the Tet-On system, transcription of an inserted gene occurs only in the presence of tetracycline or a tetracycline derivative, doxycycline. In the Tet-On system, when the tetracycline is present, a transcription factor for regulating tetracycline, tTA, binds to a tetracycline operator promoter, resulting in expression of the inserted gene.

When the expression of the inserted gene is controlled using tetracycline, gene expression capable of regulating temporal, spatial on-demand gene induction may result in an accurate, reversible and effective manner.

Accordingly, in the present invention, a gold-deposited drug reservoir capable of releasing tetracycline at a desired time in response to an electrical signal may be produced.

When the time for administration of a drug to a patient comes, smart glasses send an electrical signal, resulting in dissolution of a gold film (positive electrode), and the release of a lentivirus capable of expressing VEGFR-Fc and PDGFR-Fc from a drug reservoir as well as tetracycline. The drug reservoir may have a plurality of drug storing spaces. In one of the drug storing spaces, there may be tetracycline and a lentivirus that can be used once, and the drug reservoir may have, for example, a drug storing space that can be used for one month. The drug reservoir has micro-electro-mechanical drug delivery chips which are connected to an ASIC chip, and present in the lens.

The prepared DNA cassette was transfected into 293T cells, expression of VEGFR-Fc and PDGFR-Fc genes in the 293T cells infected with the lentivirus including the VEGFR-Fc and PDGFR-Fc genes was identified at the mRNA level (diagram on the left side of FIG. 8). In this drawing, 2.5G-AntiAMD 10 ng DNA is a positive control, and mock is a negative control, glyceraldehyde 3-phosphate dehydrogenase (GAPDH) was used as a control to see whether the experiment was or was not properly performed, for example, amplification was or was not applied in the same manner.

In addition, expression levels of VEGFR-Fc and PDGFR-Fc proteins were identified, 293T cells were infected with the lentivirus including VEGFR-Fc and PDGFR-Fc genes, and the expression of each protein in the virus was identified by an ELISA assay. The ELISA assay was carried out using a human IgG ELISA quantitation kit (E80-104, Bethyl Laboratories, Inc., U.S.A.) according to a manual included in the kit.

As shown in the graph on the right side of FIG. 8, it can be confirmed that human IgG is expressed at a high concentration of approximately 160 ng/ml in the 293T cells infected with the lentivirus including VEGFR-Fc and PDGFR-Fc genes.

The lentivirus vector prepared above was transfected into the 293T cells ($5 \times 10^5$ cells) using lipofectamine, and then the cells were cultured in each of a doxycycline (Dox)-containing medium and a doxycycline (Dox)-free medium for 48 hours. As a result of the Fc ELISA assay for identifying the expression of VEGFR-Fc and PDGFR-Fc in the culture medium, it was confirmed that, when Dox was present, Fc expression was increased to about 500 ng/ml, but when Dox was absent, Fc expression was not observed (FIG. 9). Therefore, it was verified that Tet-regulation was properly introduced.

Experimental Example 4. Identification of Lentivirus Expression in Animal Model and its Effect 8-week-old male SD rat models were divided into three groups, and their GFP expression was identified by introducing 10 µl of Lenti/GFP into a vitreous body.

In the present invention, FIG. 10 shows the result of observing the lentivirus expression in each group of the animal models by weeks (1-12 weeks (w)). Here, to correct a titer, in high, middle and low concentration groups, each ratio of Lenti/GFP infectivity was lowered by 1/100.

1 week: Fluorescence was observed throughout the retina, and stronger GFP fluorescence was observed in the high concentration group than in the other two concentration groups in the examined retina.

2 week: GFP fluorescence was exhibited stronger in the retina than the first-week retina, and observed at high levels in an inner plexiform layer (IPL) and an outer plexiform layer (OPL).

4 week: At the low and middle concentrations, results similar to those of the second week were shown, but at the high concentration, cells exhibiting green fluorescence were observed.

8 week: At the low concentration, green fluorescence became weak, and at the high concentration, expression (denoted with arrow) was observed in the cells.

12 week: Expression (denoted with arrow) was observed at the middle and high concentrations.

Therefore, the expression of the injected lentivirus was continuously observed at the middle and high concentrations for over 3 months, and retinal degeneration was observed at the high concentration. Consequently, the middle concentration was determined as a suitable concentration.

Also, to induce diabetic retinopathy in an animal model, diabetes was induced in rats in a diabetes-induced group and rats in a lentivirus-treated group expressing VEGFR-Fc and PDGFR-Fc by administering streptozoticin (Sigma, U.S.A.) at 60 mg/kg, and one week after the administration, a blood glucose concentration was measured to check if the rat had diabetes (FIG. 11).

Afterward, the rats of the lentivirus treated group expressing VEGFR-Fc and PDGFR-Fc were subjected to general anesthesia with Rompun (xylazine HCl 23.3 mg/ml, Bayer, Germany) and Zoletil 50 (Virvac, U.S.A.), and topical anesthesia with Alcaine (Proparacaine HCl 0.5%, Alcon, U.S.A.). Afterward, a drug was injected into the crystalline lens in a volume of 10 µl. Here, the lentivirus expressing VEGFR-Fc and PDGFR-Fc was administered at a concentration of $2.84 \times 10^{10}$ TU/ml. After 4 weeks of the drug administration, rats of all groups were subjected to general anesthesia, 1 ml of dextran-FITC (a mixture of 10 mg/ml of a molecule with 40 kDa and 10 mg/ml of a molecule with 10 kDa, Sigma-Aldrich, U.S.A.) was injected into the left ventricle, and then the eye ball was excised. The excised eye ball was fixed in 10% formalin, and washed with PBS. After washing, only the retina was separated, placed on a glass slide, flat-mounted, and observed using a fluorescent microscope. As a result, images were stored at a magnitude of 100×. Referring to the stored images, intensities of dextran-FITC fluorescence of normal blood vessels and peripheral blood vessels, to compare a drug effect, were compared to a normal retina. The fluorescence intensity was measured using an Image J program (ver 4.1, NIH).

As a result, according to microscopic observation of vascular leakage by VEGF, it was confirmed that vascular leakage was significantly decreased in the rats treated with the lentivirus expressing VEGFR-Fc and PDGFR-Fc, compared to a diabetes-induced group, and therefore an angiogenesis inhibiting effect in an eye exhibited by the produced lentivirus was identified (FIG. 12).

Preparation Example 5. System Including Contact Lens and Smart Glasses

In the present invention, FIG. 13 is a schematic diagram showing a production process for a smart contact lens, and energy supply and wireless communication using WiTricity.

Referring to FIG. 13 and Examples 2 and 3, the contact lens may be produced by producing a drug reservoir (FIGS. 13 (a)-(g)), combining the produced drug reservoir, an IC chip and a sensor with a transmitter coil (FIGS. 13 (h)-(j)), and adding the combined product to a lens material and molding the resultant product (FIG. 13 (k)).

Here, using a complementary-metal-oxide semiconductor (CMOS), a micro-unit integrated circuit (IC) may be formed. The maximum area of the IC is 1 mm×1 mm, and a thickness thereof is 0.2 mm.

The contact lens produced according to the present invention may receive WiTricity, and transmit data of the contact lens to a PC via an RF system.

Also, FIG. 14 shows images of the contact lens and the smart glasses, and FIG. 15 shows an outline image of the smart glasses.

The smart glasses send electrical signals wirelessly to operate the on-demand drug reservoir (drug-delivery) and sensor, and receives data via RF wireless communication. Via an ASIC chip, energy supplying may be performed using WiTricity and a photodetector, and a suitable voltage for operating a sensor for sensing NO and VEGF is transmitted.

To release a drug from the drug reservoir at a desired time, the smart glasses are able to adjust electrical signals.

Specifically, in the smart contact lens of FIG. 14, the IC may control all of the functions of the contact lens, and the WiTricity antenna is formed at an inner side of the smart lens, power may be received from the smart glasses by WiTricity through resonance, and the antenna receives power via the RF system and serves to send data (glucose concentration of the sensor, drug delivery concentration, etc.) of the smart lens to the outside through RF. In addition, a photocell may be an auxiliary battery means capable of receiving energy from solar light via a solar cell, other than WiTricity or RF, an LED may be a means for transmitting a state of the smart lens, and a photodetector may sense light emitted from the eye or outside and operate the sensor.

Also, in the smart glasses, an Eyeglass IC, which is the IC included in the glasses, may control all of the functions of the smart glasses, the WiTricity coil, which is a system for providing power to the contact lens, may deliver power to the WiTricity antenna in the smart lens at a specific frequency through resonance, and LED indicators serve to indicate a state of the contact lens or a state of the glasses, and to control a smart TV, an electronic device, or an airplane instrument panel by separate control of the signal frequency of the LED. Also, IR transceivers may serve to receive light with an IR wavelength from the sun or artificial light and charge power in a smart lens, like a solar cell.

INDUSTRIAL APPLICABILITY

In the present invention, a disease can be sensed in real time using a sensor in a contact lens, and therefore the development of a patient's disease can be more easily and rapidly identified. Also, the sensor can be used in a fluid for a long time due to high stability, and more accurately determine whether the disease should or should not treated due to high sensitivity.

The invention claimed is:

1. A contact lens for the treatment intraocular angiogenesis, comprising:
    a sensor to which a probe capable of sensing a disease marker is fixed; and
    a drug reservoir formed in a form of a drug well, which is formed at the inner side of the contact lens in contact with an eye to be indented toward the outer side thereof and sealed by an electrode pattern containing gold,
    wherein, when the disease marker is sensed by the sensor, the gold of the electrode pattern of the drug reservoir is dissolved in chlorine of the body, resulting in AuCl4-, and the drug reservoir is opened,
    the disease marker is one or more selected from the group consisting of nitrogen monoxide (NO), vascular endothelial growth factor (VEGF) and glucose,
    the drug reservoir includes a drug or a drug carrier capable of releasing a drug, and a drug releasing control substance,
    the drug is genistein or a protein drug, and the drug carrier is a viral vector expressing the protein drug,
    the viral vector is a recombinant virus produced by a recombinant vector including a DNA cassette including one or more nucleic acid sequences which encode protein drugs,
    in the DNA cassette, expression of the inserted gene is controlled by tetracycline or doxycycline.

2. The contact lens of claim 1, wherein the contact lens is based on a silicone hydrogel, poly(2-hydroxyethylmethacrylate) (PHEMA), poly(methyl methacrylate) (PMMA), poly (lactic-co-glycolic acid) (PLGA), polyvinylpyrrolidone (PVP) or polyvinylacetate (PVA).

3. The contact lens of claim 1, wherein the probe is one or more selected from the group consisting of hemin and an aptamer.

4. The contact lens of claim 1, wherein the sensor senses an occurrence of a current change when the disease marker binds to the probe.

5. The contact lens of claim 1, wherein the viral vector is one or more selected from the group consisting of a retrovirus vector, a baculovirus vector, a parvovirus vector, a Semliki Forest virus vector, a canarypox virus vector, a vaccinia virus vector, a fowlpox virus vector, a sindbis virus vector, an adenovirus vector, a piconavirus vector and an alphavirus vector.

6. The contact lens of claim 1, wherein the viral vector is a lentivirus vector.

7. The contact lens of claim 6, wherein the protein drugs are VEGFR and PDGFR.

8. The contact lens of claim 7, wherein the protein drug is an Fc-binding fusion protein.

9. The contact lens of claim 8, wherein the DNA cassette includes a nucleic acid sequence which encodes VEGFR-Fc and a nucleic acid sequence which encodes PDGFR-Fc, which are linked to transcription/translation initiation nucleic acid sequences.

10. The contact lens of claim 9, wherein the transcription/translation initiation nucleic acid sequences are internal ribosome entry site (IRES) nucleic acid sequences.

11. A method for producing a contact lens according to claim 1, including a sensor to which a probe capable of sensing a disease marker is fixed, and a drug reservoir, the method comprising:
    producing the drug reservoir by
    (a) forming a buffer layer on an amorphous silicon layer which is formed on one surface of a transparent substrate, and forming an electrode pattern containing gold on a partial surface of the buffer layer;

(b) forming a drug well layer including a drug well for accommodating a drug on the buffer layer on which the electrode pattern is not formed and the electrode pattern;

(c) stacking a plastic substrate on the drug well layer; and (d) separating the amorphous silicon layer by applying a laser beam to the surface of the transparent substrate on which the amorphous silicon layer is not formed.

12. The method of claim 11, wherein, in the step (b), after SU8 is formed on the buffer layer not having an electrode pattern and the electrode pattern, the SU8 is patterned to form a drug well having an opening, and the opening of the drug well is formed on the electrode pattern.

13. The method of claim 11, further comprising:
after step (d), patterning the buffer layer to expose the electrode pattern in contact with the drug well.

14. The method of claim 11, further comprising:
after step (d), depositing an SU8 layer on the drug well layer, and patterning the SU8 layer and the buffer layer to expose the electrode pattern in contact with the drug well.

15. The method of claim 13, wherein, when the electrode pattern is exposed by patterning the buffer layer, the electrode pattern is partially exposed.

16. A system, comprising:
a smart contact lens according to claim 1, including a sensor to which a probe capable of sensing a disease marker is fixed and a drug reservoir formed in a form of a drug well, which is formed at the inner side of the contact lens in contact with an eye to be indented toward the outer side thereof and sealed by an electrode pattern containing gold; and
smart glasses which transmit electrical signals wirelessly to control operation of the sensor and the drug reservoir of the smart contact lens.

17. The system of claim 16, wherein the sensor of the smart contact lens is operated by electrical signals transmitted from the smart glasses, and the sensor receiving the signals senses the variations in current occurring when the disease marker binds to the probe, and sends the result to the smart glasses via RF wireless communication.

18. The system of claim 16, wherein the drug reservoir of the smart contact lens is operated by electrical signals transmitted from the smart glasses, and in the drug reservoir receiving the signals, the gold of the electrode pattern sealing the drug reservoir is dissolved in chlorine, resulting in $AuCl4-$, and the electrode pattern is opened.

19. The system of claim 16, wherein power generated in a WiTricity coil of the smart glasses is received by a WiTricity antenna of the smart contact lens, and power received through control of an IC chip is used to operate the sensor and the drug reservoir.

20. The system of claim 16, wherein the smart contact lens further includes a photodetector which senses external light and converts the light into electricity.

21. The system of claim 16, wherein the smart contact lens further includes a photocell for auto powering.

* * * * *